United States Patent
Hoelzl

(10) Patent No.: US 9,240,040 B2
(45) Date of Patent: Jan. 19, 2016

(54) METHOD AND SYSTEM FOR PREDICTING ERRORS ON COMPONENTS OF ROTATING MACHINES BY THERMOGRAPHY

(75) Inventor: Roland Hoelzl, München (DE)

(73) Assignee: Prüftechnik Dieter Busch AG, Ismaning (DE)

(*) Notice: Subject to any disclaimer, the term of this patent is extended or adjusted under 35 U.S.C. 154(b) by 464 days.

(21) Appl. No.: 13/809,985

(22) PCT Filed: Jul. 12, 2011

(86) PCT No.: PCT/DE2011/001454
§ 371 (c)(1),
(2), (4) Date: Mar. 18, 2013

(87) PCT Pub. No.: WO2012/010154
PCT Pub. Date: Jan. 26, 2012

(65) Prior Publication Data
US 2013/0169799 A1  Jul. 4, 2013

(30) Foreign Application Priority Data
Jul. 13, 2010  (DE) .................. 10 2010 027 072

(51) Int. Cl.
*G06T 7/00* (2006.01)
*G01N 25/72* (2006.01)
*G01N 25/00* (2006.01)

(52) U.S. Cl.
CPC .............. *G06T 7/0004* (2013.01); *G01N 25/72* (2013.01); *G01N 25/00* (2013.01)

(58) Field of Classification Search
CPC .............................. G01N 25/72; G06T 7/0004
USPC .................... 374/4, 5; 702/130; 382/141
See application file for complete search history.

(56) References Cited

U.S. PATENT DOCUMENTS

| | | | |
|---|---|---|---|
| 4,854,162 A | 8/1989 | Yerace et al. | |
| 5,032,727 A | 7/1991 | Cox, Jr. et al. | |
| 7,528,372 B2 | 5/2009 | Garvey, III et al. | |
| 7,706,596 B2 | 4/2010 | Garvey | |
| 7,732,768 B1 | 6/2010 | Haigh et al. | |
| 7,809,258 B2 | 10/2010 | Strandemar et al. | |

(Continued)

FOREIGN PATENT DOCUMENTS

| | | |
|---|---|---|
| CN | 1546960 A | 11/2004 |
| WO | 2004/097389 A2 | 11/2004 |
| WO | 2004/097389 A3 | 11/2004 |

OTHER PUBLICATIONS

Second Office Action, State Intellectual Property Office of the People's Republic of China dated Nov. 15, 2014, corresponding Chinese Patent Application No. 201180034525.1, English translation.

(Continued)

*Primary Examiner* — Fabio Lima
(74) *Attorney, Agent, or Firm* — Roberts Mlotkowski Safran & Cole, PC; David S. Safran

(57) ABSTRACT

Computer-based detection of damage on machine components, such as misalignments and mechanical damage on bearings and clutches, is achieved using mathematical linkage of the temperatures of selected regions of thermography pictures. Photographs from the visible spectral range can be consulted in the computed-based detection.

14 Claims, 1 Drawing Sheet

(56) References Cited

U.S. PATENT DOCUMENTS

| | | | |
|---|---|---|---|
| 2002/0172410 A1* | 11/2002 | Shepard | 382/141 |
| 2004/0120383 A1* | 6/2004 | Kennedy et al. | 374/57 |
| 2007/0087311 A1* | 4/2007 | Garvey et al. | 434/21 |
| 2009/0010635 A1* | 1/2009 | Strandemar et al. | 396/133 |
| 2009/0161720 A1* | 6/2009 | Pelletier | 374/4 |
| 2010/0100275 A1 | 4/2010 | Mian et al. | |
| 2010/0131225 A1 | 5/2010 | Carlson | |

OTHER PUBLICATIONS

Condition Monitoring and Diagnostics of Machines—Thermography—Part 1: General Procedures; In Draft International Standard ISO; Jan. 1, 2005; XP55012370, pp. 4-23; Listed on International Search Report Filed Jan. 14, 2013 for This Application.

* cited by examiner ically provides that the thermography pictures are
compared in regular intervals. The intervals here are
chosen such that hardly any changes of the operating
state which have a major effect on the temperature of
the monitored components can be expected. The invention
is based on the finding that detection of misalignment of a
clutch is possible by using thermography especially when
the operating state of the machine has hardly changed
during recording of the reference picture and recording
of the current picture.

METHOD AND SYSTEM FOR PREDICTING ERRORS ON COMPONENTS OF ROTATING MACHINES BY THERMOGRAPHY

BACKGROUND OF THE INVENTION

1. Field of the Invention

The invention relates to a method and a system which is used for detection of misalignment and for prediction of faults on rotating machines and their components by means of thermography.

2. Description of Related Art

Various methods are known for predicting faults on rotating machines and their components, such as bearings, and the alignment of motors. Simplest is visual inspection in which obvious damages are sought. These damages are the emergence of oil or lubricating grease or visible leaks. In visual inspection fill levels of storage tanks, but also the accumulation of material in filters are also monitored.

Vibration analysis was developed from acoustic inspections which are carried out in part with a stethoscope. In doing so, vibration signals are recorded with microphones or accelerometers. Mostly piezosensors which are also made as MEMS modules are used nowadays as accelerometers. A signal for vibration rate or displacement can be obtained from the acceleration signal of the accelerometer by single or double integration. Thus, the original frequency range of the acoustic inspections is expanded from what is audible to ultrasound. Moreover, mathematical and digital methods can be used by further electronic processing in the evaluation of the data of vibration measurement, such as, for example, Fourier analysis.

Another method is oil analysis. While this method is relatively revealing, it is associated with high cost because, on the one hand, an oil sample must be taken, and on the other, the samples must be sent to a laboratory; this entails great time expenditure.

Another method which is being increasingly used in practice is thermography. Here, a picture of a machine component of interest is taken with an infrared camera. Often, photographs in the visible spectral range are superimposed on these pictures; the photographs have been taken from a similar or the same perspective, for example, the infrared camera and the camera for the visible spectral range being integrated in a housing. Thus, U.S. Pat. No. 7,809,258 describes such a camera with a technique for superimposing pictures from the visible and infrared spectral range. The evaluation of the photographs is reserved to the human observer who is often limited to finding especially striking temperature values in the infrared picture. This method is helpful to quickly locate, for example, a bearing which has run hot or a clutch which has become hot due to misalignment, and to initiate corrective measures. This location-finding of components which have become hot, however, is only possible when a human observer correctly determines the component which has become hot in the infrared picture. Thus, U.S. Pat. No. 7,706, 596 mentions (in column 5 in lines 54-60) that it is necessary that an observer must have certain skills for the evaluation of infrared pictures.

Approaches to machine evaluation of infrared pictures are described in U.S. Pat. No. 7,528,372. There, the superposition of infrared pictures and photographs in the visible spectral range is mentioned. A comparison of thermography photographs which is carried out with computers is, in general terms, described as a "thermal performance algorithm". Little is given concerning the specific execution of these algorithms.

These algorithms can be applied to thermography photographs which have been taken at long time intervals, such as, for example, a picture of a new machine and a picture of the same machine after it has been in operation for a long period of time. Changing ambient conditions, such as the temperature in the factory hall in which the machine has been set up, engender problems in discovering these algorithms. Other problems are changes of operating conditions which are due to different operating states of the machine and also to the temperature of the medium to be conveyed changing in a pump which is driven by a motor, for example.

It is often possible to manage with artificially induced full load of a machine system which is to be assessed when the system has been subjected to initial start-up or maintenance and then to take a thermography picture. To check the machine at a later time, again full load is artificially produced and a thermography picture is taken. These two thermography pictures are then compared by experienced evaluators. This method is expensive and of little reliability due to the artificial inducement of the full load and the limited availability of experienced evaluators. It depends on the experience and ability of the evaluator whether and to what extent parameters, such as, for example, the ambient temperature or the amount and/or the temperature of a conveyed medium are correctly taken into account.

SUMMARY OF THE INVENTION

The object of the invention is to provide a method and system which enables comparison of infrared pictures of components of rotating machines which have been taken at different times and to give a specific algorithm for execution.

This object is achieved by a method and a system as described herein. In particular, the object is achieved by a reference state being acquired with the infrared camera in a picture, and on the other hand, a picture which has been taken after a certain operating interval being compared to this reference picture. The comparison is made not by an evaluator, but by a computer system.

In the construction of a machine, sites or components can often be recognized which are subject to special loads in later operation, and therefore, which must be carefully monitored. Moreover, in the operation of a machine, for certain components, problems often arise again and again which justify subjecting the respective component to special monitoring. Examples of these components are clutches or rolling bearings, for example, for shafts.

Clutches are often used between a motor and a machine component which is driven by this motor, such as a fan or a pump for conveying a fluid medium. Here, the geometrical alignment of the motor to the pump or to the fan plays a major part for the loading of the clutch and the bearings of the shafts which are connected to this clutch. When the relative alignment of the motor to the pump or to the fan has not been done correctly or over time a displacement of the two components occurs, this can remain unnoticed for a long time and can lead to catastrophic damage. It is relatively complex to attach an alignment device to machines at regular time intervals because this is normally only possible when the system is shut down. Continuous monitoring of the geometrical alignment state of a rotating clutch is difficult due to the attachment of the alignment device because this attachment is only possible on machine components which are not moving. To reduce the cost of a machine shutdown which is necessary for checking the alignment state, in accordance with the invention thermography photographs are taken. Misalignment appears as heating of one region of the clutch in the thermography picture.

The subject matter of the invention is to evaluate the different heating of individual components by machine, therefore with a computer, the effects which different operating parameters or different ambient conditions have on the temperature of the respective component being taken into account. To achieve this, after start-up of a new machine or after successful maintenance, at least one thermography picture is taken which is used as a reference. In the choice of the view, it must be watched that components are visible which are subject to particular loads, such as, for example, the aforementioned clutches or bearings. These views are established based on the construction of the machine or based on experience with earlier maintenance of this machine or other machines of the same design. In establishing the views, it is helpful if the manufacturer of the machine or its components makes available data of a thermal simulation which is often carried out especially in serial products. It can be necessary to make bores in coverings or housings in order to attach the objective lens or lenses of the thermography camera to the machine, such being accommodated with a camera for the visible spectral range in a housing such that it is possible to record the selected views. It is also advantageous, after establishing a view, to attach a fastening device for the camera to the camera location chosen for this view if this is possible without adversely affecting operation. In this way, it is ensured that the same location is always chosen for the photograph.

After selecting the views, heat sources and heat sinks are identified in the reference picture. Heat sinks are, for example, foundations or articles visible in the respective view which are closely related to the ambient temperature. For a fan, this is, for example, also the conveyed fluid medium. It is also possible to attach marks or labels in the region visible to the camera; they become visible in the picture as objects as are at the ambient temperature. The picture regions on which the objects are visible are in a close relationship to the ambient temperature, are called cold sites and can be used as references.

For heat sources, it must be distinguished between those sources whose special heating is to be monitored when a problem occurs, and those sources which in normal operation already have an elevated temperature. Heat sources which are to be monitored for the case of the occurrence of a problem are called first hot sites. Examples of this heating include motor losses, friction on the clutch and bearing friction. Heat sources which occur in normal operation and which can be used as a reference like cold sites are called second hot sites. When a fan or a pump is imaged, the conveyed fluid medium can be both a heat source and also a heat sink. Examples of first hot sites are therefore bearings, clutches and motors.

In the establishment of heat sources and heat sinks. Therefore. the heat flows which occur in the picture between these sources and sink must be considered. Thus, the cold, first hot and second hot sites are then identified using the machine components to which they are assigned. In the establishment of the cold, first hot and second hot sites, a thermal simulation is helpful as also mentioned above in conjunction with the establishment of views. In the reference picture and in the thermography picture which is taken at a later time, the pixels which are assigned to these sites and which will be generally groups of pixels are then identified.

At this point, in accordance with the invention, by producing a mathematical linkage between the temperatures of cold sites corresponding to one another in the reference picture and in a thermography picture taken at a later time, a relation between these two pictures for purposes of normalization is conveyed. A human observer has, therefore, been necessary in the past for evaluation because this normalization is not undertaken. For example, is all pixels of the thermography picture taken at a later time at higher ambient temperature are reduced in their temperature by the amount of the difference between the temperatures of a cold site in the reference picture and the same cold site in the picture taken at a later time, this normalization is achieved in its simplest form. The accuracy of this normalization can be increased by the temperature of several cold sites being considered, therefore being included in the mathematical linkage. In addition the temperatures of second hot sites—both in the reference picture and also in a thermography picture taken at a later time—can also be considered in the mathematical linkage. These temperatures of the second hot sites can depend on operating parameters, as becomes clear below using the figures.

DETAILED DESCRIPTION OF THE INVENTION

For purposes of illustration, a covering over the clutch region has been removed on a machine and two thermography pictures with good and bad alignment have been taken. The color scale of the original pictures was converted into gray-scale values in FIGS. 1 & 2, white corresponding to the highest measured temperature and black corresponding to the lowest measured temperature.

Figure 1:
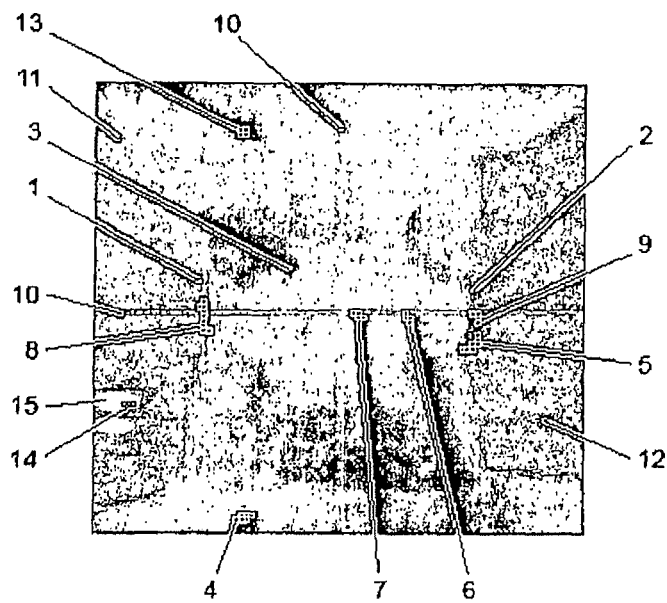
FIG. 1 is thermography picture of a machine with good alignment for use as the reference.
Figure 2:
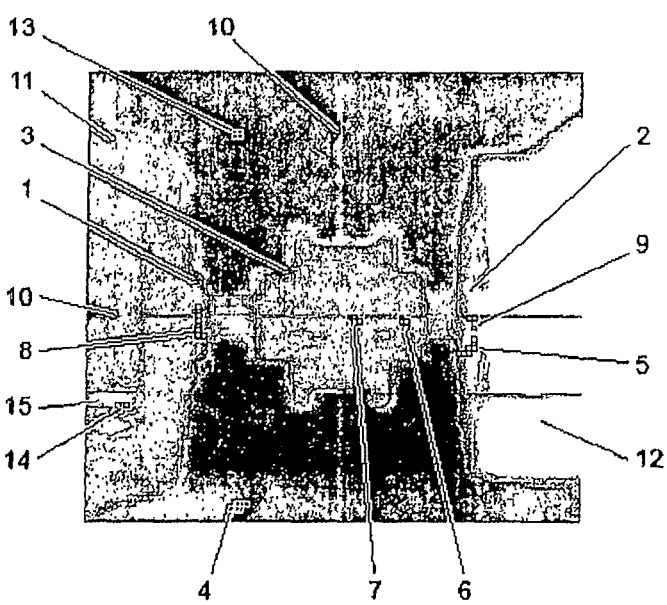
FIG. 2 is thermography picture corresponding to that of FIG. 1, but being of a machine with poor alignment.

FIG. 1 contains the thermography picture with good alignment and is used as the reference. At left, the motor 11 is recognizable, and at the right, the driven pump 12 or the driven fan. In this photo, the clutch 3 cannot be very clearly recognized. In FIG. 2, which contains the thermography picture with poor alignment all relevant components are clearly visible. The shaft of the motor is mounted in the bearing 1 on the motor on the side facing the clutch, the shaft of the driven unit is mounted in the bearing 2. The clutch which connects the two shafts is labeled with reference number 3.

On the base plate which is exposed to relatively small thermal loads, several pixels which are labeled with reference number 4 are identified. This group of pixels constitutes a region in which there is a temperature which deviates only slightly from the temperature of the vicinity or even corresponds to the temperature of the ambient air. Therefore, this region constitutes a cold site. Another cold site in the picture background is identified with reference number 13. For example, it can be the wall of the space in which the measurement is taken. In the regions 6, 7 of the clutch 3, several pixels were established as regions in which a temperature rise occurs at intensified mechanical loads. These regions constitute first hot sites.

In the bearing 1, another first hot site 8 is identified, and in the bearing 2, first hot sites 5, 9 are identified. Moreover, another second hot site 15 is detectable on the motor 11 in FIGS. 1 and 2. Some pixels 14 were established as a hot reference site at second hot site 15. This hot site 15 is an opening of the motor 11 in which an increased temperature occurs. This temperature of the hot site 15 is also a measure for the load state and the power consumption of the motor 11. Therefore, it can be referenced directly to the operating parameters of the machine.

A reticle 10 is attached in the objective lens of the thermography camera and is visible in the photographs. With this reticle, the connecting line of the two shafts is located. The vertical line of the reticle was aligned to the center line of the clutch by the viewfinder of the infrared camera. Depending on the version of the camera, it can also be provided that another sighting mark becomes visible in the viewfinder of the camera and in the photo instead of a reticle.

Thus for example, there can be a laser in the camera housing whose beam direction corresponds to the viewing direction of the objective lens of the camera. With this laser, it is possible to direct the user to site a certain conspicuous point on the machine with the laser beam. This sighting mark. on the one hand. enables quick visual checking whether the correct vantage point for the photo has been found, and on the other hand, for a correct location of the sighting mark on the object the assignment of the individual pictures upon superposition is facilitated, both for a human observer and also for the computer system in the evaluation, especially with respect to the required storage space and the required computation cost.

A comparison of FIG. 1 with FIG. 2 shows that the misalignment causes heating both of clutch 3 and also its connections to the two shafts. Moreover, heating of the pump 12 and of the two bearings 1, 2 is clearly visible. In order to enable digital evaluation of these two pictures at this point, different regions of interest are established in these pictures which are advantageously prepared as digital photographs. The reference here is, first of all, the cold site 4 which is identified in both pictures. In a computer system, the temperature of the cold site 4 in the thermography picture of FIG. 2, which is called the first thermography picture, is determined. Likewise, the temperature of the cold site 4 in the thermography picture of FIG. 1 which is being used as the reference is determined if this has not already been done at an earlier time. A normalization of FIG. 2 with reference to FIG. 1 is now also possible with the aid of a mathematical linkage of these two temperatures. Thus, the temperatures of all pixels of FIG. 2 can be subtractively changed by the temperature difference between the cold site 4 in FIG. 1 and the cold site 4 in FIG. 2. This temperature difference therefore enables balancing of the temperatures from FIG. 1 and FIG. 2. As a result of this normalization, the machine components which are visible in FIG. 2 have the same temperature as the same machine components in FIG. 1 when they are in comparable states and are not subjected to special loads.

If at least one other cold site 13 has been established, it is possible to average the temperature difference over several cold sites in the mathematical linkage. Moreover, it can be useful to also provide one or more second hot sites 15 as a reference. Based on this reference or these references, the thermography picture of FIG. 2 which was taken at a later time is compared to the reference picture of FIG. 1 by means of a mathematical method.

This normalization of thermography pictures which have been taken at different times under different ambient and operating conditions is carried out in a computer system in accordance with the invention. On the one hand, it is possible to transmit thermography pictures, and optionally, pictures from the visible spectral range out of the camera into the computer which can also be a laptop, a notebook, a handheld or a cell phone. On the other hand, this computer can also be integrated into a corresponding camera system. This camera system can also contain only an infrared camera. However, it is also possible for this camera system to contain both an infrared camera and also a camera for the visible spectral range.

In accordance with the invention, this computer system is provided with a database in which thermography pictures are stored. Other data are also recorded into this database. These data include pictures from the visible spectral range, the operating parameters of the machine and its components, ambient temperatures and characteristics of the machine and its components. Together with these data and the photographs, the times at which these data were collected are also stored.

The normalization of the individual thermography pictures using corresponding references is arranged, in accordance with the invention, by a mathematical linkage of the temperatures of these sites. In the simplest case, this mathematical linkage is subtractive, the temperature difference of the cold sites 4 in FIGS. 1 and 2 being subtracted.

In the reference picture, if a second hot site has been established as a reference, a useful mathematical linkage arises with the inclusion of the temperature difference of the second hot sites, one each in FIGS. 1 and 2, and the temperature difference of the cold sites, again one each in FIGS. 1 and 2. The quotient of these temperature differences can now be normalized for its part relative to the temperatures of the cold site in FIG. 2, the reference.

Likewise, it is possible to individually determine the temperature differences between the second hot site and cold site for each of the pictures of FIGS. 1 and 2, and to form the quotient of these temperature differences. Again, normalization to the temperature of the cold site in FIG. 2 is possible.

In one configuration of the invention, the picture of FIG. 2, which was taken at a later time, is normalized by the mathematical linkage in each individual pixel to the reference picture.

In one especially advantageous configuration of the invention, this normalization is performed only for selected regions which are chosen, for example, in the establishment of the views.

Other relations in the mathematical linkage are also useful beyond the formation of differences and quotients between the individual temperatures. The functional relationship between the ambient temperature and the cold site or the cold sites is advantageous here. It is also favorable if the functional dependency of the temperature of the second hot site on one or more operating parameters of the machine is included in the mathematical linkage. This functional dependency exists, for example, between the temperature of the hot site 15 and the power consumption of the motor 11. Other functional dependencies exist, for example, with reference to the speed of the motor 11 or of the pump 2, and the temperature and/or the amount of the medium which has been conveyed with the pump 2. Likewise, of course, the emissivities of the imaged surfaces can be included in the observed temperatures and can be considered in the mathematical linkage. These emissivities can be changed, for example, by deposits on the components being examined.

In the preceding text, some examples for operating parameters were named, such as the power consumption of the motor. It goes without saying that this power consumption is only one example of a host of possible operating parameters, such as also the indicated temperature of the conveyed medium. For conductive elements, such as fuses, the power consumption can be such a parameter. For moving machine elements, the existing amount of lubricant can be another parameter. Likewise, the aforementioned clutches and bearings can be regarded only as examples for machine components.

At this point, it is useful to evaluate the database with several stored thermography pictures and the pertinent operating parameters in order to empirically find the relationship between the operating parameters and the temperature values of the stored cold and hot sites. Moreover, when there is a defect or a misalignment, a respective thermography picture can be taken before and after correcting this defect or the misalignment, stored in the database, and correlated accordingly with the pertinent operating parameters. The result of this evaluation is now stored in the database. Thus, over time, extensive databases are formed which make it possible when a newly taken thermography picture is available to draw conclusions about whether there is damage, and if yes, what type of damage it is, or whether new damage and/or a new misalignment is incipient. Thus, this invention can be incorporated into a predictive maintenance plan. In addition, the diagnosis measures in this maintenance plan are simplified because a thermography photograph can be quickly and easily prepared, while a vibration measurement and its evaluation or a re-alignment of the machine components need only be undertaken when something conspicuous appears in the thermography picture.

When the pictures are stored in the database in the computer system, it is useful to treat the image data such that a common vantage point of the observer is established for several pictures. Therefore, individual pictures are corrected such that pictures always arise on which the same articles appear at the same sites. Thus, the pixels or pixel groups which are stored for the cold and hot sites can be located at the same sites in the individual pictures so that they are more easily accessible to a mathematical evaluation. The demand for storage space for the database is also reduced in this way.

This type of storage is especially advantageous when pictures of different resolution are to be combined with one another. Pictures of different resolution can arise when, on the one hand, different camera types are used for the thermography pictures or when a thermography camera is used together with a camera for the visible spectral range.

It is not necessary to store the database for the thermography pictures in the camera itself and in a special computer system, although this is, of course, one embodiment of the invention. It is also possible to expand a database which is present in the control of the machine or in the control board of several machines such that the data which have been collected in addition with the invention can be stored there. This configuration of the invention is especially advantageous because operating data, such as individual operating parameters, are already stored in an existing database. These individual operating parameters can be, for example, the power consumption of the motor or the speed of the pump.

It is especially advantageous if these superimposed pictures which can comprise, besides the infrared, also the visible spectral range, are reproduced after completed normalization in a false color display on the display of the computer system. A new overall picture is produced by means of the mathematical linkage. Thus, components which merit special attention appear especially emphasized. Moreover, it is possible to connect a temperature deviation of certain components to a certain type of defect. A heated clutch in conjunction with heated bearings, as in the figures, indicates a misalignment so that when a heated clutch and a heated bearing are present an additional display, for example, in text form or as a voice output, can take place which indicates that, at this point, the alignment of the motor relative to the pump or to the housing should be checked and corrected if necessary. Accordingly, another display or voice output is useful which indicates incipient bearing damage when a bearing is heating up, if the clutch is not heated. This display or voice output contains correction instructions which can be, for example, the checking of the lubricant reservoir or a vibration measurement to be taken. In a third case, when only the clutch is hot, but not the bearings, there is very probably only damage on the clutch. The corresponding display or voice output then recommends replacement of the clutch the next time that the machine is shut down.

One special advantage of the invention lies in that a superimposed representation of thermography pictures and pictures in the visible spectral range in which problematic components are especially emphasized in the described manner enables especially clear reproduction of the machine state.

Based on construction data or simulation data as are determined by the manufacturer of a fan or a pump, in a CAD system in the design of the machine, the first hot sites can also be established after establishing the aforementioned views for the photographs in the expected thermography picture and can be stored in the database together with characteristics of the assigned machine components.

In one advantageous configuration of the invention, when the views are established all visible components of the machine are identified and pertinent data are stored in the database. Thus, in the evaluation of the database and the newly taken thermography pictures, the computer and the software for evaluation using stored data of machine components when a new first hot site becomes visible in the thermography picture itself can identify the pertinent components without an intervention of a human observer being necessary.

One advantageous application of the invention is thermal growth. It is generally considered difficult to correctly align, for example, a unit consisting of a motor and pump since this alignment conventionally takes place in the cold state. When the machine reaches its normal operating state with elevated temperatures of the motor and pump, the relative positioning of the motor relative to the pump changes since the motor and pump, in the normal case, are subject to different thermal expansions. The determination of a favorable alignment state is facilitated at this point in that in a thermography picture elevated temperatures on the clutch and bearings become easily visible and accessible to computer evaluation. Thus, for example, in test runs at a manufacturer of such a combination of a motor and pump, different alignment states for a cold machine can be set. In each alignment state, the machine is put into operation and a thermography photograph is taken. With the invention, it is now possible to determine with computer support using thermography pictures that alignment state in which the heating of clutch and bearings is least. At the final location of the machine, in accordance with the invention, it is possible to determine an alignment state for a particular operating state using thermography photographs in which the heating of the clutch and bearings is least. This determined operating state can be, for example, the one which occurs most frequently. The invention also enables simple monitoring of the success of an alignment measure or the comparison of the alignment state in different operating states.

In another useful configuration of the invention, it is possible to take a thermography picture at regular time intervals, for example, hourly. For this purpose, the thermography camera can remain on the aforementioned fastening device between the recording times. From this collection of thermography pictures, critical states or incipient faults can be determined with computer support with the aid of operating parameters and recording times which are stored at the same time.

What is claimed is:

1. A method for determining the state of components of a machine by evaluation of thermography pictures, comprising the steps of:
    comparing at least one first thermography picture to at least one reference thermography picture obtained previously,
    assigning at least one first pixel or group of pixels in the at least one first thermography picture and in the at least one reference thermography picture as at least one cold site,
    wherein normalization of the at least one first thermography picture is performed with the result of a mathematical linkage of the temperatures of the at least one cold site in the at least one first thermography picture and in the at least one reference thermography picture, and
    wherein after said normalization, at least one second pixel or group of pixels is identified in the at least one first thermography picture as at least one first hot site and compared to the at least one reference thermography picture and assigned to a certain machine component.

2. The method as claimed in claim 1, comprising the further step of drawing a conclusion about the state of the machine component which has been assigned to the first hot site.

3. The method as claimed in claim 1, wherein in the at least one first thermography picture and the at least one reference thermography picture, at least one second hot site is assigned to at least a respective third pixel or group of pixels whose temperature enables a conclusion about an operating parameter of the machine, and wherein the temperature of at least one second hot site is included in the mathematical linkage of the temperatures of the at least one cold site in the first thermography picture and the at least one reference picture.

4. The method as claimed in claim 1, wherein ambient temperature is included in the mathematical linkage of the temperatures of the at least one cold site in the first thermography picture and the at least one reference thermography picture.

5. The method as claimed in claim 1, wherein operating parameters of the machine are included in the mathematical linkage.

6. The method as claimed in claim 1, wherein the first thermography picture and the at least one reference thermography picture are superimposed before assignment of the pixel or groups of pixels to one of the cold and hot sites such that cold and hot sites coincide on the superimposed pictures.

7. The method as claimed in claim 6, wherein a picture from the visible spectral range is additionally superimposed in the superposition of the at least one first thermography picture and the at least one reference thermography picture.

8. The method as claimed in claim 6, wherein a sighting mark is considered in the superposition of the at least one first thermography picture and the at least one reference thermography picture.

9. The method as claimed in claim 8, wherein the sighting mark is produced with a laser beam.

10. The method as claimed in claim 8, wherein the sighting mark is produced by a reticle.

11. The method as claimed in claim 1, wherein at least one of a clutch which connects two shafts to one another and a rolling bearing is used as the machine component.

12. The method as claimed in claim 1, wherein a database stores reference values for at least one of cold and hot sites, operating parameters, ambient temperatures and state variables of the respective machine components and emissivities of the surfaces of the respective machine components.

13. The method as claimed in claim 12, wherein the database stores previously obtained thermography pictures and pictures from the visible spectral range.

14. The method as claimed in claim 13, wherein results of the mathematical linkage and the pictures which have been stored in the database are superimposed and the result of the superposition is displayed to a user as a result picture.

* * * * *